United States Patent [19]

Berg

[11] Patent Number: 5,453,167
[45] Date of Patent: Sep. 26, 1995

[54] SEPARATION OF XYLENES BY EXTRACTIVE DISTILLATION

[75] Inventor: Lloyd Berg, 1314 S. Third Ave., Bozeman, Mont. 59715

[73] Assignee: Berg; Lloyd, Bozeman, Mont.

[21] Appl. No.: 418,382

[22] Filed: Apr. 7, 1995

[51] Int. Cl.⁶ .................. B01D 3/40; C07C 7/08
[52] U.S. Cl. .................. 203/57; 203/51; 203/56; 203/60; 203/63; 203/65; 203/67; 585/805; 585/808; 585/860; 585/864; 585/866
[58] Field of Search .................. 203/51, 56, 60, 203/65, 57, 63, 67; 585/805, 808, 860, 864, 866

[56] References Cited

U.S. PATENT DOCUMENTS

| | | | |
|---|---|---|---|
| 2,494,274 | 1/1950 | Woerner | 203/57 |
| 2,721,170 | 10/1955 | Johnson | 203/57 |
| 4,673,465 | 6/1987 | Berg et al. | 203/57 |
| 5,039,380 | 8/1991 | Berg | 203/60 |
| 5,091,059 | 2/1992 | Berg | 203/60 |
| 5,094,723 | 3/1992 | Berg | 203/56 |
| 5,094,725 | 3/1992 | Berg | 203/60 |

*Primary Examiner*—Wilbur Bascomb, Jr.

[57] ABSTRACT p-Xylene cannot be separated from m-xylene by distillation or rectification because of the proximity of their boiling points. p-Xylene can be separated from m-xylene by means of extractive distillation. Effective agents are 3-ethylphenol and isopropyl palmitate. Effective agents for separating mixtures of p-xylene, m-xylene and o-xylene are 2-butoxyethyl acetate and 1,1,1-trichloroethane.

1 Claim, No Drawings

SEPARATION OF XYLENES BY EXTRACTIVE DISTILLATION

FIELD OF THE INVENTION

This invention relates to a method for separating xylenes using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

p-Xylene, B.P.=138.4° C. and m-xylene, B.P.=139.1° C. have a relative volatility of only 1.02 and are virtually impossible to separate by conventional distillation or rectification. o-Xylene boils at 144.5° C. and the relative volatility between m-xylene and o-xylene is 1.12. Extractive distillation would be an attractive method of effecting the separation of p-xylene from m-xylene and o-xylene if agents can be found that (1) will enhance the relative volatility between p-xylene, m-xylene and o-xylene and (2) are easy to recover from the xylenes, that is, form no azeotrope with the xylenes and boil sufficiently above the xylenes to make recovery by rectification possible with only a few theoretical plates. The advantage of using extractive distillation in this separation can be seen from the data shown in Table 1. If an agent can be found that will increase the relative volatility to 1.3, 99% purity p-xylene from m-xylene can be obtained with only 47 actual plates.

TABLE 1

Theoretical And Actual Plates Required vs. Relative Volatility For Xylene Separation

| Relative Volatility | Theoretical Plates Required At Total Reflux, 99% Purity | Actual Plates Required, 75% Eff. |
|---|---|---|
| 1.02 | 465 | 620 |
| 1.08 | 120 | 160 |
| 1.10 | 97 | 129 |
| 1.12 | 89 | 119 |
| 1.14 | 71 | 95 |

TABLE 1-continued

Theoretical And Actual Plates Required vs. Relative Volatility For Xylene Separation

| Relative Volatility | Theoretical Plates Required At Total Reflux, 99% Purity | Actual Plates Required, 75% Eff. |
|---|---|---|
| 1.18 | 56 | 75 |
| 1.20 | 51 | 68 |
| 1.30 | 35 | 47 |
| 1.40 | 28 | 37 |
| 1.50 | 23 | 31 |
| 1.60 | 20 | 27 |

OBJECTIVE OF THE INVENTION

The objects of this invention are to provide a process or method of extractive distillation that will enhance the relative volatility of p-xylene to m-xylene in their separation in a rectification column. It is a further object to provide a process of extractive distillation that will enhance the relative volatility of p-xylene, m-xylene and o-xylene when these three occur in a mixture. Another object of this invention is to identify organic compounds that are stable, can be separated from the xylenes by rectification with relatively few plate and can be recycled to the extractive distillation column with little decomposition.

TABLE 2

Effective Agents For Separating p-Xylene From m-Xylene

| Compounds | Relative Volatility |
|---|---|
| None | 1.02 |
| o-Cresol | 1.14 |
| 3-Ethyl phenol | 1.30 |
| 2,4-Dimethyl phenol | 1.18 |
| 3-Ethyl phenol, 2-Nitro phenol (mixture) | 1.23 |
| 3-Ethyl phenol, 2,6-Dimethyl phenol (mixture) | 1.25 |
| 2,4-Dimethyl phenol, 2-Nitro phenol (mixture) | 1.21 |
| 2,4-Dimethyl phenol, 4-Nitro phenol (mixture) | 1.30 |
| 3-Methoxy ethyl cyano acetate | 1.16 |
| Isopropyl palmitate | 1.16 |
| Methyl salicylate | 1.15 |
| n-Butyl cyano acetate | 1.19 |

TABLE 3

Effective Agents For Separating The Three Xylenes

| | Relative Volatility | | |
|---|---|---|---|
| Compounds | p-Xylene/ m-Xylene | p-Xylene/ o-Xylene | m-Xylene/ o-Xylene |
| 2-Butoxyethyl acetate | 1.1 | 1.6 | 1.5 |
| 1,1,1-Trichloroethane | 1.08 | 1.18 | 1.1 |

SUMMARY OF THE INVENTION

The objects of the invention are provided by a process for the separation of p-xylene from m-xylene which entails the use of certain organic compounds which will enhance the relative volatility of p-xylene from m-xylene. Also provided are agents that will enhance the relative volatility of p-xylene, m-xylene and o-xylene when they occur in mixtures.

DETAILED DESCRIPTION OF THE INVENTION

I have discovered that certain organic compounds will enhance the relative volatility of p-xylene from m-xylene. They are listed in Table 2. The effective agents are o-cresol, 3-ethyl phenol, 2,4-dimethyl phenol, 3-ethyl phenol+2-nitro phenol, 3-ethyl phenol+2,6-dimethyl phenol, 2,4-dimethyl phenol+2-nitro phenol, 2,4-dimethyl phenol+4-nitro phenol, 1,1,1-trichloroethane, 1,1,2-trichloroethane, 2-butoxyethyl acetate and n-butyl cyano acetate.

Table 3 lists the compounds that are effective in enhancing the relative volatility when the three xylenes occur as a mixture. They are 2-butoxyethyl acetate and 1,1,1-trichloroethane.

THE USEFULNESS OF THE INVENTION

The usefulness or utility of this invention can be demonstrated by referring to the data presented in Tables 1, 2 and 3. All of the successful agents show that p-xylene can be separated from m-xylene by means of extractive distillation in a rectification column and that the ease of separation as measured by relative volatility is considerable. Also included are two agents that will increase the relative volatility of p-xylene, m-xylene and o-xylene from mixtures.

WORKING EXAMPLES

Example 1:

Twenty-four grams of p-xylene, six grams of m-xylene and 60 grams of 3-ethyl phenol were charged to a vapor-liquid equilibrium still and refluxed for four hours. Analysis indicated a vapor composition of 81.4% p-xylene, 18.6% m-xylene; a liquid composition of 76.9% p-xylene, 23.1% m-xylene which is a relative volatility of p-xylene to m-xylene of 1.3.

Example 2:

Seventy-five grams of p-xylene and 75 grams of m-xylene were placed in the stillpot of a 5.5 theoretical plate glass perforated plate rectification column and heated. When refluxing began, an extractive agent comprising 3-ethyl phenol was pumped into the column at a rate of 20 ml/min. The temperature of the extractive agent as it entered the column was 130° C. After establishing the feed rate of the extractive agent, the heat input to the column was adjusted to give a total reflux rate of 40 ml/min. After 1.5 hours of operation, overhead and bottoms samples were collected and analysed. The overhead composition was 51.5% p-xylene, 48.5% m-xylene and the bottoms analysis was 34.4% p-xylene, 65.6% m-xylene. Using these compositions in the Fenske equation, with the number of theoretical plates in the column being 5.5, gave an average relative volatility of p-xylene to m-xylene of 1.15 for each theoretical plate.

Example 3:

Ten grams of p-xylene, 10 grams of m-xylene, 10 grams of o-xylene and 60 grams of 2-butoxyethyl acetate were charged to the vapor-liquid equilibrium still and refluxed for 13 hours. Analysis indicated a vapor composition of 43.6% p-xylene, 35.4% m-xylene and 21.0% o-xylene; a liquid composition of 37.2% p-xylene, 33.1% m-xylene and 29.7% o-xylene. This is a relative volatility of p-xylene to m-xylene of 1.10, for p-xylene to o-xylene of 1.6 and for m-xylene to o-xylene of 1.5.

I claim:

1. A method for recovering p-xylene from a mixture of p-xylene and m-xylene which comprises distilling a mixture of p-xylene and m-xylene in the presence of from one to ten parts by weight of an extractive agent per part of p-xylene-m-xylene mixture, recovering the p-xylene as overhead product and obtaining the m-xylene and the extractive agent as bottoms product, wherein said extractive agent consists of one material selected from the group consisting of o-cresol, 3-ethyl phenol, 2,4-dimethyl phenol, 2,6-dimethyl phenol, 2-nitro phenol, 4-nitro phenol, isopropyl palmitate, 3-methoxy ethyl cyano acetate, methyl salicylate and n-butyl cyano acetate.

* * * * *